United States Patent [19]

Urdea et al.

[11] Patent Number: 5,552,280
[45] Date of Patent: Sep. 3, 1996

[54] HYDROPHOBIC NUCLEIC ACID PROBES

[75] Inventors: Michael S. Urdea, Alamo; Thomas Horn, Berkeley, both of Calif.

[73] Assignee: Chiron Corporation, Emeryville, Calif.

[21] Appl. No.: 384,630

[22] Filed: Feb. 6, 1995

Related U.S. Application Data

[63] Continuation of Ser. No. 64,357, May 18, 1993, abandoned, which is a continuation of Ser. No. 855,448, Mar. 19, 1992, abandoned, which is a continuation of Ser. No. 374,462, Jun. 30, 1989, abandoned.

[51] Int. Cl.$^6$ .................... C07H 21/02; C07H 21/04; C12Q 1/68
[52] U.S. Cl. ................ 435/6; 514/44; 536/22.1; 536/25.32; 935/77; 935/78
[58] Field of Search .................. 435/6; 536/25.32, 536/22.1; 514/44; 935/77, 78

[56] References Cited

U.S. PATENT DOCUMENTS

| | | | |
|---|---|---|---|
| 4,379,843 | 4/1983 | Cashion | 435/178 |
| 4,455,370 | 6/1984 | Bartelsman et al. | 435/6 |
| 4,493,899 | 1/1985 | Smith et al. | 436/508 |
| 4,588,682 | 5/1986 | Groet et al. | 435/6 |
| 4,716,103 | 12/1987 | Hunger et al. | 435/5 |
| 4,806,546 | 2/1989 | Carrico et al. | 536/27 |
| 4,868,105 | 9/1989 | Urdea et al. | 435/6 |
| 4,925,921 | 5/1990 | Avrameas et al. | 530/389 |

FOREIGN PATENT DOCUMENTS

| | | |
|---|---|---|
| 3824110 | 1/1990 | Germany. |
| WO90/10448 | 9/1990 | WIPO. |

OTHER PUBLICATIONS

Rubin et al., *J. Immunol. Methods* (1983) 63:359–366.

*Primary Examiner*—W. Gary Jones
*Assistant Examiner*—Paul B. Tran
*Attorney, Agent, or Firm*—Kenneth M. Goldman; Robert P. Blackburn

[57] ABSTRACT

A polynucleotide which has been modified by a hydrophobic moiety so that the polynucleotide attaches to a substrate by the hydrophobic moiety, rather than by a portion of the polynucleotide, thereby allowing the polynucleotide to be available for hybridization.

4 Claims, 1 Drawing Sheet

HYDROPHOBIC NUCLEIC ACID PROBES

CROSS-REFERENCE TO RELATED APPLICATIONS

This application is a continuation of U.S. Ser. No. 08/064,357, filed on May 18, 1993, now abandoned, which is a continuation of U.S. Ser. No. 07/855,448, filed on Mar. 19, 1992, now abandoned, which is a continuation of U.S. Ser. No. 07/374,462, filed on Jun. 30, 1989, now abandoned, All of the referenced applications are incorporated herein by reference in full.

DESCRIPTION

1. Technical Field

This invention is in the fields of biochemical assays and nucleic acid chemistry. More particularly, it relates to novel nucleic acid multimers having hydrophobic moiety(ies) for substrate attachment.

2. Background of the Invention

Nucleic acid hybridization is commonly used in biochemical, biomedical, and genetic research. Nucleic acid hybridization has found commercial application in clinical diagnostic assays.

Nucleic acid hybridization assays contain the basic elements of single-stranded analyte nucleic acid (either DNA or RNA) which is hybridized to a labeled nucleic acid probe; the resulting labeled duplexes are detected. Labels may be either radioactive or nonradioactive. This general scheme has had various modifications made to it in order to facilitate the separation of the duplexes to be detected from extraneous materials and/or to amplify the signal that is detected.

Antibody detection assays using nucleic acid may be done, for example, in microtiter dish wells. Unlike the immunoassay, in which a peptide antigen or antibody is "passively adsorbed" to the polystyrene surface through hydrophobic interaction, nucleic acids do not bind efficiently to a substrate surface such as polystyrene. Despite this problem, one reported method (Pisetsky and Peters (1981) J. Immunol. Meth. 41:187–200; also U.S. Pat. No. 4,493,899 (sepharose binding)) involved binding large fragments of DNA to microtiter dishes in order to measure serum antibodies against DNA, which is symptomatic of the autoimmune disease lupus erythematosus. Another method of binding DNA to a microtiter dish well used ultraviolet irradiation to sensitize the polystyrene surface. Zovali and Stollar (1986) J. Immunol. Meth. 90:105–110.

Although these methods may have been successful in antibody detection assays, they have not been as useful for nucleic acid hybridization assays. The reason is that in an immunoassay the interaction between an antibody and an antigen involves about 5 amino acids, which is a very small portion of the molecule. In contrast, nucleic acid hybridization can involve 6 to 300,000 or more nucleotides. Often the entire length of the nucleic acid probe is needed for maximal sensitivity and specificity, such as when entire polynucleotides are hybridized and small differences in hybridization are detected.

The known methods of attaching nucleic acids to substrates are not useful in nucleic acid hybridization assays because the binding of nucleic acid to substrate is non-specific (see FIG. 1). These random portions and lengths of the nucleic acid that bind to the substrate are no longer available for hybridization. The problem is not confined to polystyrene microtiter dish wells. Similar difficulties have been encountered when binding DNA to nitrocellulose.

DISCLOSURE OF THE INVENTION

In the present invention, a polynucleotide is attached to a hydrophobic moiety thereby permitting the polynucleotide to bind to a substrate by the hydrophobic moiety leaving its full length available for assays. (See FIG. 2.) By providing a hydrophobic attachment point at one end of the polynucleotide, the polynucleotide is bound to the substrate at the attachment point rather than by the polynucleotide itself. This increases the sensitivity and flexibility of nucleic acid assays by allowing more of the polynucleotide to be available for hybridization. More flexibility in assay design is also provided by allowing polynucleotides to bind to a number of unmodified or unsubstituted surfaces, such as microtiter dishes, nylon, nitrocellulose, glass, and other passive adsorption materials.

The present invention is directed to a polynucleotide capture probe for binding a target polynucleotide in a sample, wherein said capture probe comprises a hydrophobic moiety capable of noncovalently binding to a substrate, which hydrophobic moiety is bound to a polynucleotide sequence complementary to said target nucleotide.

Another aspect of the present invention provides methods to synthesize and incorporate hydrophobic molecular functions into polynucleotides. These functions render a portion of the polynucleotide hydrophobic and therefore capable of binding to substrates, such as polystyrene microtiter dish wells.

Another aspect of the present invention is methods of using the polynucleotides having hydrophobic molecular functions, such as in detection assays and purification assays.

MODES OF CARRYING OUT THE INVENTION

Definitions

Figure 1:
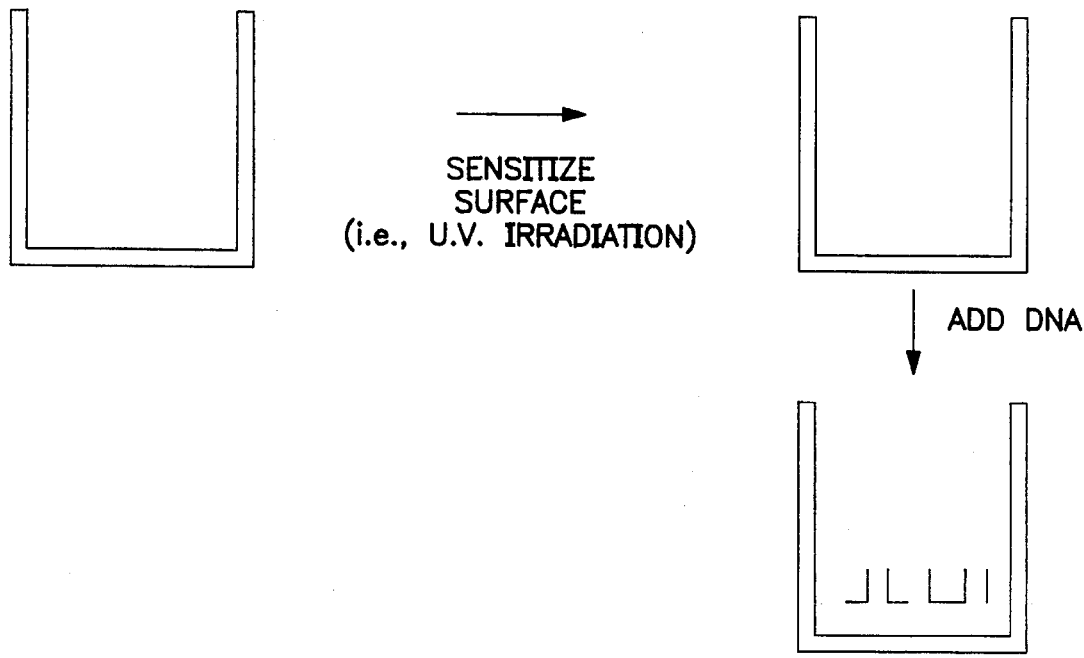
FIG. 1 diagrammatically illustrates DNA binding using UV-activation of the substrate, as disclosed in the prior art.
Figure 2:
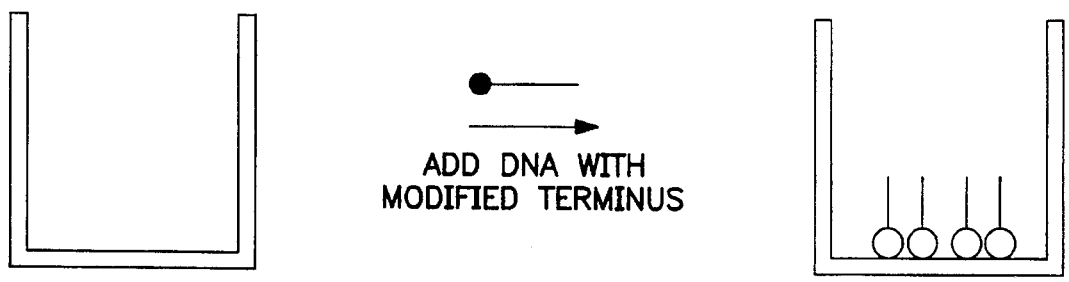
FIG. 2 diagrammatically depicts the method of the invention.

The terms "hydrophobic group" and "hydrophobic moiety" are used interchangeably herein and refer to any group capable of covalently binding to a polynucleotide sequence and noncovalently binding to a substrate while remaining bound to the substrate during reaction conditions. The hydrophobic moiety may also include a spacer or linker region intermediate between the hydrophobic moiety and the polynucleotide sequence. The spacer or linker can comprise a polypeptide, organic molecule, oligonucleotide, or other suitable linker.

The term "oligonucleotide" as used herein refers to a short polynucleotide sequence of two to about ten nucleotides.

The term "polynucleotide" as used herein refers to a molecule which may be comprised of RNA, DNA, modified nucleotides, or combinations thereof, but usually will be single-stranded DNA. The length of the polynucleotide will usually be about 12 to about 150 nucleotides, most commonly about 20 nucleotides. The upper limit is determined by the length of polynucleotide that is capable of being synthesized; the lower limit is determined by the sensitivity required in the assay.

The term "label" as used herein refers to any atom or molecule which can provide a detectable (preferably quantifiable) signal, and which can be attached to a polynucleotide. Labels may provide a detectable signal of fluorescence, radioactivity, colorimetry, x-ray diffraction or absorption, magnetism, enzymatic activity, and the like. Suitable labels include fluorophores, chromophores, radioactive atoms, electron-dense reagents, enzymes, and ligands having specific binding partners. "Specific binding partners" are molecules capable of binding to a ligand molecule with a high degree of specificity. For example, a monoclonal antibody (MAb) and its specific antigen; biotin and avidin or streptavidin; IgG and protein A, as well as other receptor-ligand pairs known in the art. Enzymes are typically detected by their enzymatic activity. For example, horseradish peroxidase (HRP) is usually detected by its ability to convert 3,3',5,5'-tetramethylbenzidine (TMB) to a blue pigment, quantifiable with a spectrophotometer. This description is not meant to categorize the various labels into distinct groups since the same label may function in more than one mode. $^{125}$I, for example, may serve as either a radioactive label or as an electron-dense reagent. HRP may serve as an enzyme or as an antigen for a MAb. In addition, labels may be combined to achieve a desired effect. MAbs and avidin also require labels so that one might label a polynucleotide with biotin and detect its presence with avidin labeled with either $^{125}$I or with an anti-biotin MAb labeled with HRP. A labeled MAb to dsDNA (or hybridized RNA) could directly detect the presence of hybridization without labeling the nucleic acids. Other possible schemes will be readily apparent to those of ordinary skill in the art, and are considered to be equivalents within the scope of the invention disclosed herein.

General Method

Synthesis of Polynucleotide and Hydrophobic Group

Any polynucleotide may be modified with the hydrophobic moieties of the present invention. Useful polynucleotides will contain, or be suspected of containing, the particular nucleic acid sequence desired. The nucleic acid(s) may be obtained from natural sources or may be synthesized by means known in the art.

General methods for synthesizing uncharged nucleotide derivatives to facilitate passage through cell membranes have been reported. Miller et al. (1986) Biochem. 25:5092–5097; Agris et al. (1986) Biochem 25:6268–6275. These nucleotide derivatives often employ a methyl protecting group, which is not particularly stable to the deprotection reagents used to remove the other protecting functions that are typically used in DNA synthesis.

The polynucleotides for use with the present invention may be either linear or branched polynucleotides. These polynucleotides can have identical, repeating single-stranded oligonucleotide units or different single-stranded oligonucleotide units. The sequence, length, and composition of at least one of the units will permit binding to a single-stranded nucleotide sequence of interest, such as an analyte or a polynucleotide bound to the analyte. To achieve the appropriate binding specificity and stability the polynucleotide unit may be at least two, will usually be at least six, more usually about 12, and most commonly about 22–40 nucleotides in length. The polynucleotide unit should be long enough to hybridize specifically to a target polynucleotide.

Specific polynucleotides include those used as the capture probe in solution phase sandwich assays, as disclosed in commonly-owned U.S. Ser. No. 06/807,624, filed 11 December 1985, now U.S. Pat. No. 4,268,105 the disclosure of which is incorporated by reference. Binding these oligonucleotides to the substrate by an end (either 3' or 5') using the hydrophobic groups of the invention results in the entire length being available for hybridization.

Alternatively, the polynucleotide may be a multimet having a linear or branched structure, as shown in the copending, commonly owned application, U.S. Ser. No. 340,031, filed 18 April 1989. The disclosure of this and related copending applications are incorporated by reference herein.

No single method of preparing the polynucleotide for use in the present invention is contemplated. The polynucleotide may be prepared by chemical cross-linking techniques, direct chemical synthesis, cloning, enzymatic assembly, a combination thereof, or any other suitable methodology. When prepared by cloning, nucleic acid sequences that encode the entire multimet or fragments thereof can be made in single- or double-stranded form by conventional cloning procedures. Alternatively, the polynucleotide is produced by using as a template a polynucleotide having a base sequence complementary to the target sequence. If the polynucleotide is double stranded, the strands must be separated before they can be used.

Strand separation is done either as a separate step or simultaneously with the synthesis. For example, strand separation can be accomplished by any suitable denaturing method, including physical, chemical, or enzymatic means. One physical method of separating the nucleic acid strands involves heating the nucleic acid until it is completely (more than 99%) denatured. Heat denaturation typically is done in the range of about 80° to 105° C. for a period of about one to ten minutes. Strand separation may also be enzymatically induced by a hellcase enzyme, or an enzyme capable of exhibiting hellcase activity, e.g., the enzyme RecA, which has hellcase activity and, in the presence of riboATP, is known to denature DNA. Conditions suitable for strand separation using helicase enzymes are described by Kuhn Hoffmann-Berling, *CSH-Quantitative Biology*, 43:63 (1978), and techniques for using RecA are reviewed in C. Radding, *Ann. Rev. Genetics*, 16:405–36 (1982).

Single-stranded polynucleotides may be cloned using conventional single-stranded phage vectors, such as M13. Fragments may be linked enzymatically or chemically to form the polynucleotide. If enzymatically linked, a ligase such as T4 DNA ligase may be used. If the nucleotide is to be chemically cross-linked, the individual units may be synthesized with one or more nucleic acids which are derivatized to have functional groups that provide linking sites for cross-linking or branching; alternatively, derivatization to provide linking sites can occur after synthesis. A preferred chemical cross-linking procedure is described in commonly owned copending U.S. patent application Ser. No. 945,876, filed 23 December 1986, the disclosure of which is incorporated herein by reference.

When prepared by direct chemical synthesis, polynucleotides (which may contain derivatized nucleic acids whose functional groups are blocked) are made by conventional polynucleotide synthesis techniques. If derivatized nucleic acids are used, the functional groups are unblocked and oligonucleotide units are synthesized out from the unblocked site(s).

Alternatively, one may prepare polynucleotides by other known methods in the art as, for example, in U.S. Pat. No. 4,603,195, the contents of which are incorporated by reference herein.

It is believed that many different hydrophobic moieties can be employed and attached to a polynucleotide sequence in the present invention. A number of modification schemes could be used to achieve similar binding characteristics. In general, however, the hydrophobic moiety will have various general characteristics. When covalently bound to the polynucleotide sequence, the hydrophobic moiety will be able to bind noncovalently to a substrate and remain bound under reaction conditions (e.g., under wash and hybridization conditions). In order to achieve such binding to the substrate, the number of hydrophobic groups that need to be bound to the polynucleotide will be in the general range of one to about ten, preferably about three to seven, most preferably about five. Since, however, the function of the hydrophobic moiety is to provide a method of noncovalently anchoring a polynucleotide to the substrate, the exact number and mixture of hydrophobic moieties is not critical so long as this function is accomplished.

In general, the hydrophobic moiety will be essentially non-polar, no more than sparingly soluble in water or aqueous solutions, and have a core structure in the range of $C_{12}$ to about $C_{50}$, which may be linear, branched, cyclic, or aromatic. This core structure may comprise for example (without limitation) such aromatic moieties, as naphthalene, anthracene, or phenanthrene; such cyclic moieties as decahydronaphthalene; and linear or branched moieties, such as elcosane. The hydrophobic moiety will have at least one functional group capable of covalently binding, or being modified so that it may covalently bind, to a polynucleotide sequence.

If desired, the polynucleotides of the present invention may be labeled. Labels can include, for example, radiolabeling at the 5' end of the polynucleotide using $^{32}P$-ATP and kinase. Other suitable labels, such as fluorescent dyes, electron-dense reagents, enzymes, ligands having specific binding partners, etc. can be used.

Once the polynucleotides of the present invention are bound to hydrophobic moieties, whether or not a label is used, they are ready to be used in a variety of different assay schemes, depending upon the type of assay that is necessary to achieve the desired results. For example, the polynucleotide (attached to a hydrophobic group) may be bound to substrate. This substrate may comprise a number of materials in a variety of forms. Substrate materials can comprise polystyrene, nylon, nitrocellulose, or glass. The substrate may be formed, without limitation, as microtiter or other dishes, fibers, tubes, beads, dipsticks, wells, filters, membranes, etc.

The polynucleotide, which is bound to the substrate, may be overcoated to reduce non-specific binding. Overcoating may be done using a number of molecules, such as bovine serum albumin (BSA), salmon sperm DNA, etc.

Any number of assay methods may be used, the preferred methods being disclosed in commonly owned, copending applications, U.S. Ser. Nos. 340,031 (supra), U.S. Pat. No. 4,868,105, the disclosure of which is incorporated by reference herein, or by direct sandwich assay.

The following examples of the invention are offered by way of illustration and not by way of limitation.

EXAMPLES

The preferred embodiment of the present invention uses a hydrophobic protecting group, which is relatively stable to the normal deprotection chemistry on the phosphite (and subsequently phosphate) of a thymidine nucleotide. The incorporation of five uncharged 3'-O-[2-(1-naphthyl)ethoxy] phosphorylthymidine residues to the 5' end of the capture probe, CACCACTTTCTCCAAAGAAG, renders it sufficiently hydrophobic to bind to a microtiter dish surface.

Preparation of Hydrophobic Nucleotide (A) 2-(1-Naphthalene)ethanol (available commercially, e.g., from Aldrich Chemical Co.) (3.95 g, 23 mmole) was dissolved in 180 ml acetonitrile and evaporated to dryness in vacuo to remove all moisture from the 2-(1-Naphthalene)ethanol. The residue was dissolved in 100 ml dry acetonitrile and then added dropwise to a stirred solution of $PCl_3$ (8.7 ml, 100 mmole) in 100 ml acetonitrile under argon while the flask was cooled to 0° C. The ice bath was then removed and stirring was continued for 1 hour @20° C. The solvent and excess $PCl_3$ were removed in vacuo by repeated coevaporation with $CH_3CN$ (3×100 ml) to give 5.5 g crude 2-(1-naphthalene)ethoxy dichlorophosphine (1).

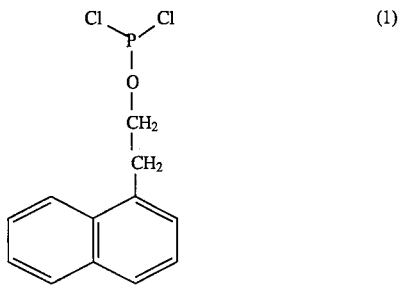

This crude product was dissolved in 50 ml dry $CH_3CN$ under argon and N,N-diisopropyl trimethylsilylamine [Aldrich] (27 mole, 1.8 g, 4.8 ml) was added dropwise with stirring @20° C. and the stirring continued for one hour @20° C. The solvent was then removed in vacuo and the volatile residuals were removed by coevaporation with dry acetonitrile (2×100 ml) to give the product in quantitative yield (20 mmole). The crude 2-(1-naphthalene)ethoxy-chloro-N,N-diisopropylamino phosphine (2) was used without further purification.

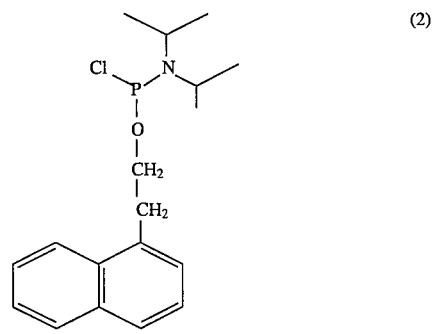

A solution of 5'-dimethoxythitylthymidine (9 mmole) in 50 ml of $CH_2Cl_2$ containing N,N-diisopropylethylamine (18 mmole, 3.1 ml) was cooled to 0° C. with an external ice bath. The flask was flushed with argon and 12 mmole of (2) in 30 ml of $CH_2Cl_2$ was added dropwise with stirring over about 5 minutes. Stirring was continued for 30 min. TLC analysis showed the reaction to be complete. Then 500 ml of ethyl acetate was added and the combined organic phase was washed with 80% saturated aq. NaCl (2×500 ml). After drying of the organic phase over solid $Na_2SO_4$ for 30 minutes, the solution was filtered and evaporated to dryness. The resulting residue was dissolved in 100 ml of toluene and then evaporated to dryness. The treatment was repeated with acetonitrile. The resulting foam was dissolved in 40 ml of toluene and added to a rapidly stirred solution of 600 ml hexane cooled externally with dry ice. The precipitate was rapidly collected by filtration and dried for 18 hours at reduced pressure to give 6.35 g of white powder of 5'-dimethoxytritylthymidine-3'-O-2-(1-naphthalene)ethoxy-N,N-diisopropylaminophosphine (3) (83% yield).

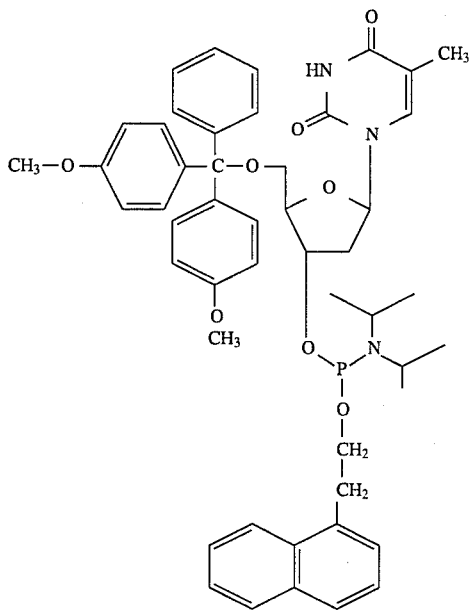

(3)

(B) Proceeding as in part (A) above, but sustituting 5'-dimethoxytritylcytidine, 5'-dimethoxytritylguanosine, or 5'-dimethoxytrityladenosine, the corresponding hydrophobic nucleotides are prepared.

(C) Proceeding as in part (A) above, but substituting 5'-dimethoxytritylcytidine, 5'-dimethoxytritylguanosine, 5'-dimethoxytrityladenosine, or 5'-dimethoxytrityluridine, the corresponding hydrophobic 2'-O-protected ribonucleotides are prepared.

Preparation of Hydrophobic Capture Probe

A solution of 3 (0.1M in acetonitrile) was used to prepare
5'-HO(T-P*)$_5$=CACCACTTTCTCCAAAGAAG*-3'

(4), [Where P* = OPO$_2$
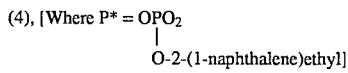
O-2-(1-naphthalene)ethyl]

on solid support using standard phosphoramidite chemistry.

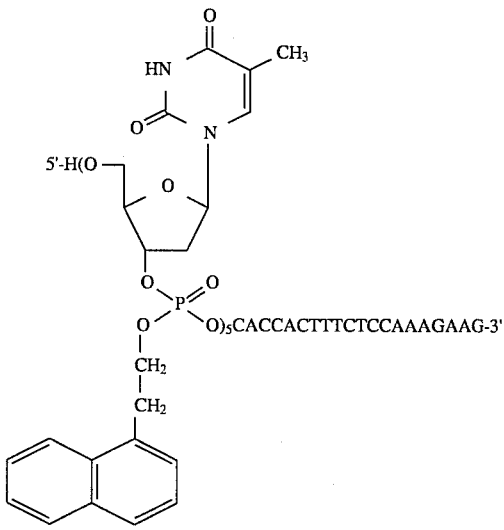

(4)

Deprotection was accomplished with 2.5% DCA in $CH_2Cl_2$ for 2 min, thiophenol/triethylamine/dioxane (v/v/v; 1:1:2) for 1 h at 20° C., then concentrated aqueous $NH_4OH$ for 24 h at 20° C. The product was evaporated to dryness. PAGE analysis of a small aliquot showed one major band and a few shorter minor bands. The fully deprotected material was used for microtiter dish coating without further purification.

Microtiter Dish Coating Procedure

Method A: A 50 µl aliquot of a solution containing 2 nanomoles of the capture probe in 1 ml of 50 mM MES (pH=5.4), 1×PBS (pH=7), or 0.1M sodium borate (pH=9.3) was added to white Microlite I or clear Immulon II microtiter wells (both from Dynatech Inc., Chantilly, Va.). After 18 hours at room temperature, the plate was washed with 0.1×SSC, 0.1% SDS. After incubation with an additional 380 µl aliquot of the wash solution, the plate was washed several times with 1×PBS.

Microtiter Dish Binding Capacity Assessment

A 5' $^{32}$P-labeled complement to the capture probe was prepared by standard procedures and placed in 1×HM (0.1% SDS, 4×SSC, 1 mg/ml sonicated salmon sperm DNA, 1 mg/ml poly-A, 10 mg/ml BSA) at a concentration of 200 pmoles/ml. A 50 µl aliquot was placed in each well and set at 55° C. for 1 hour. A control well that had not been coated with DNA was also employed.

Results

| Coating procedure | Well type | Total counts |
|---|---|---|
| MES | Clear | 2,913 ± 661 |
| MES | White | 1,413 ± 364 |
| PBS | Clear | 10,364 ± 1120 |
| PBS | White | 1,849 ± 277 |
| Borate | Clear | 17,573 ± 2725 |
| Borate | White | 2,631 ± 106 |
| Control | Clear | 160 ± 157 |
| Control | White | 677 ± 96 |

The borate coating procedure is presently the best method. Under these coating conditions, undetectable quantities of bound capture probe without the hydrophobic nucleotide addition are observed. These levels of binding are approximately 10% of those typically obtained with the polyphenylalanyl lysine coating procedure of U.S. Ser. No. 340,031 supra.

Method B: The coating procedure was followed as in Method A, above, except the coating reaction was 36 hours instead of 18 hours. Microlite I Removawells (Dynatech) were employed.

*Neisseria gonorrhoeae* pilin assay

The pilin gene assay was performed using the plasmid control as described in U.S. Ser. No. 340,031 (supra). Briefly, the plasmid pHE63, which is composed of the entire 3.2 kb HBV genome, cloned into the EcoRI site of plasmid pBR325 linearized with EcoRI and diluted into normal human serum, was used as the standard analyte. Samples were run in triplicate and read on a Dynatech microtiter dish luminometer.

Results

| Target Concentration | Relative Luminescence |
|---|---|
| 100 attomoles | 0.78 ± 0.10 |
| 20 attomoles | 0.23 ± 0.03 |
| 0 | 0.05 ± 0.00 |

Commercial Utility

The modified polynucleotides of the present invention may be marketed separately or already attached to a substrate. When attached to a substrate, they may be sold in kit form and used for a number of assay procedures. These assays could include both clinical diagnostic tests and research applications.

Modifications of the modes described above for carrying out the invention that are obvious to those of skill in the art are intended to be within the scope of the following claims.

What is claimed:

1. A polynucleotide capture probe for binding a target polynucleotide in a sample to a substrate, wherein said capture probe comprises:

at least one hydrophobic moiety capable of noncovalently attaching to an unsubstituted substrate selected from the group consisting of glass, nylon, polystyrene, and nitrocellulose; and a polynucleotide covalently bound to said at least one hydrophobic moiety, wherein said at least one hydrophobic moiety is selected from the group consisting of a naphthalene moiety, a decahydronaphthalene moiety, and a non-polar $C_{12}$ to $C_{50}$ moiety that is linear, branched, cyclic or aromatic.

2. A nucleic acid hybridization assay reagent which comprises the polynucleotide capture probe of claim 1 attached to an unsubstituted substrate selected frown the group consisting of glass, nylon, polystyrene, and nitrocellulose.

3. The polynucleotide capture probe of claim 1 wherein the at least one hydrophobic moiety is separated from the polynucleotide by a spacer selected from the group consisting of polypeptide and polymethylene.

4. The polynucleotide capture probe of claim 1 wherein the at least one hydrophobic moiety comprises at least one 1-naphthyl group attached to a phosphate moiety on the polynucleotide through an ethylene linkage.

* * * * *